(12) United States Patent
Glossop et al.

(10) Patent No.: US 8,041,412 B2
(45) Date of Patent: Oct. 18, 2011

(54) SYSTEM FOR IMAGE-GUIDED ENDOVASCULAR PROSTHESIS AND METHOD FOR USING SAME

(75) Inventors: Neil David Glossop, Toronto (CA); Bradford Johns Wood, Potomac, MD (US)

(73) Assignees: Koninklijke Philips Electronics N.V., Eindhoven (NL); The United States of America, as represented by the Secretary DHHS, Washington, DC (US)

( * ) Notice: Subject to any disclaimer, the term of this patent is extended or adjusted under 35 U.S.C. 154(b) by 1002 days.

(21) Appl. No.: 11/761,134

(22) Filed: Jun. 11, 2007

(65) Prior Publication Data

US 2008/0015677 A1    Jan. 17, 2008

Related U.S. Application Data

(60) Provisional application No. 60/812,121, filed on Jun. 9, 2006.

(51) Int. Cl.
*A61B 5/05* (2006.01)

(52) U.S. Cl. ........................................... 600/424

(58) Field of Classification Search .................. 600/407, 600/410, 414, 423, 424; 623/1.11, 1.15, 623/1.34
See application file for complete search history.

(56) References Cited

U.S. PATENT DOCUMENTS

| | | | |
|---|---|---|---|
| 6,726,712 B1 * | 4/2004 | Raeder-Devens et al. ... | 623/1.11 |
| 6,785,571 B2 | 8/2004 | Glossop | |
| 7,550,001 B2 * | 6/2009 | Dorn et al. ................... | 623/1.12 |
| 7,697,972 B2 * | 4/2010 | Verard et al. .................. | 600/424 |
| 2003/0028233 A1 * | 2/2003 | Vardi et al. ................... | 623/1.11 |
| 2005/0018319 A1 | 1/2005 | Yano | |
| 2006/0282147 A1 * | 12/2006 | Andreas ........................ | 623/1.11 |
| 2007/0032862 A1 * | 2/2007 | Weber et al. .................. | 623/1.34 |
| 2009/0299174 A1 * | 12/2009 | Wright et al. ................. | 600/424 |

* cited by examiner

*Primary Examiner* — Tse Chen
*Assistant Examiner* — Rochelle Reardon

(57) ABSTRACT

Systems and methods for obtaining position sensor space data regarding an endovascular prosthesis within an anatomical region of a patient include at least one position indicating element which is movable within an endovascular prosthesis is tracked by a tracking system. A guidance portion of the endovascular prosthesis constrains movement of position indicating elements within the endovascular prosthesis.

19 Claims, 7 Drawing Sheets

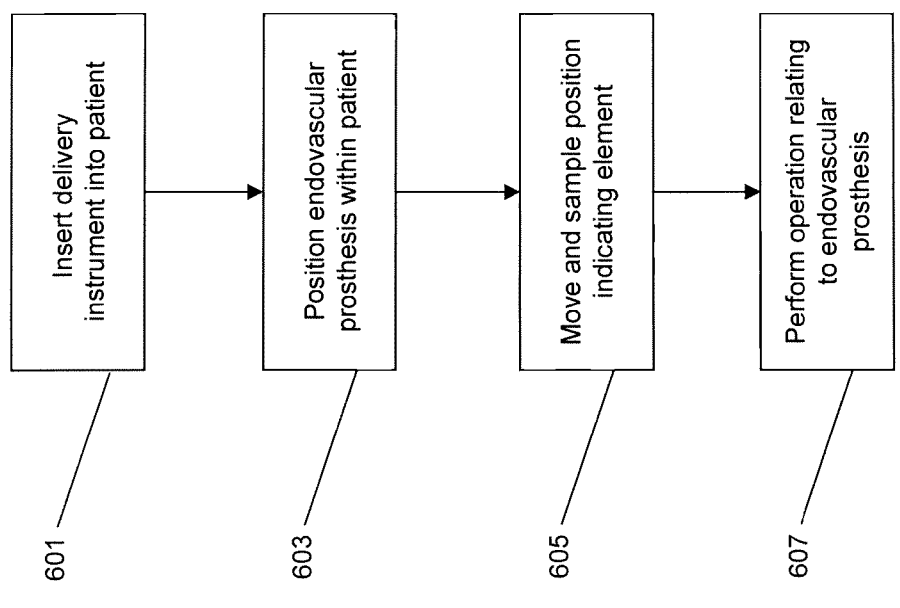

SYSTEM FOR IMAGE-GUIDED ENDOVASCULAR PROSTHESIS AND METHOD FOR USING SAME

RELATED APPLICATIONS

This application claims priority to U.S. Provisional Patent Application Ser. No. 60/812,121, filed Jun. 9, 2006, which is hereby incorporated by reference herein in its entirety.

STATEMENT OF GOVERNMENT RIGHTS

The Government of the United States of America may have certain rights in the invention disclosed and claimed below.

FIELD OF THE INVENTION

This invention relates to a system for an image-guided endovascular prosthesis placement device that includes position sensing elements movable between two or more positions relative to an endovascular prosthesis as well as a method for using the image-guided endovascular prosthesis placement device.

BACKGROUND OF THE INVENTION

Stents, grafts, covered stents, vascular endoprostheses, struts or other endovascular devices of various shapes, sizes, and materials are generally used as therapy for minimally invasive treatment of various conditions such as, for example, vascular aneurysms (especially in the aorta) atherosclerotic plaque at risk for rupture, vascular occlusion, stenosis, or other indications. These endovascular devices may be made of various materials such as, for example, PolyTetraFluoro-Ethylene (PTFE or Teflon) with Nickel-Titanium (nitinol), stainless steel, and/or other material.

Placement of such endovascular devices is generally performed with x-ray guidance, often a portable C-arm fluoroscopy system that can be wheeled into an operating room for monitoring the location of the device before and during deployment. Exact positioning is crucial to successful outcomes. Placement errors as small as one millimeter may result in stroke, thrombus (clot), or "endoleak" (i.e., where blood leaks around the outside of the graft and into the aneurysm), making the therapy ineffective and potentially dangerous.

For example, knowledge of the exact location of vessels that branch off the aorta (such as carotid artery, renal arteries, celiac artery) may be critical to the success of placement of an endovascular device. As such, treatment planning often involves detailed measurements of aortic diameter at multiple locations, as well as an assessment of exact length of a graft or device required. Consideration as to location of calcium and atherosclerotic plaque is also given, so that severely diseased segments of the aorta may be avoided as potential landing spots. Furthermore, there is relatively little information currently available on where the spinal and lumbar arteries arise in relation to an aneurysm, and there is a relatively high incidence of damage to the spinal cord, which may result in paralysis and paresis as direct complications of a placement procedure.

Therefore, the ability to directly use pre-operative imaging such as, for example, Computed Tomography Angiography (CTA), Magnetic Resonance Angiography (MRA), and x-ray angiography, or other imaging during stent or stent/graft placement may improve the accuracy of the placement procedure by giving real-time feedback of location of branch vessels and enabling minor adjustments to avoid covering or landing a strut or fold of an endovascular device in critical vessels, calcium, or plaques. Other advantages may also be realized with the direct use of pre-operative imaging during placement procedures.

Current techniques involve confirming device location after placement of the device in its non-deployed state. This is generally done with angiography and conventional vessel road mapping, or plain fluoroscopy with reference to bones. However, there is little to no ability to correct for breathing or cardiac cycle motion during the deployment. It is therefore difficult both to plan the ideal deployment location and to carry out accurate placement according to the plan.

Current standard training videos and training modules show no roadmapping at all, or roadmapping without dynamic referencing. Some widely used training materials show an "expert" surgeon drawing on a monitor with a marker pen to show where the surgeon wants to place the endovascular device in relation to an x-ray fluoroscopic image that does not have vessels opacified.

Furthermore, referencing during endovascular device procedures is often performed by comparing bony landmarks on 2-dimensional x-ray images. However, this does not accurately reflect the exact location of target structures or non-target structures at any given point in time, which increases the inaccuracy of placement procedures.

These and other problems exist in current techniques.

SUMMARY OF THE INVENTION

In some embodiments, the systems and methods of the invention enable tracking endovascular prostheses and/or patient structures using electromagnetic (EM) or other tracking systems that track one or more position indicating elements. In some embodiments, the invention also enables determination of multiple locations within an endovascular prosthesis through the use of trackable position indicating elements that are selectively movable within the body of an endovascular prosthesis.

In some embodiments, the invention uses tracking systems to obtain position sensor space data regarding endovascular prostheses and instrumentation used therewith. This position sensor space data may enable enhanced/accurate placement, deployment, and modification of endovascular prostheses as well as providing other features. For example, in some embodiments, use of a tracking system enables dynamic referencing during placement and deployment of an endovascular prosthesis which may enable correction for breathing motion, cardiac motion, or other motion. Additionally, position sensor space data received from tracking systems may be used for planning purposes, to determine if significant motion exists above a specified threshold that may positively or negatively affect the device, to compensate for motion, and/or for other purposes.

In some embodiments, the invention includes a system for image guided placement and deployment of an endovascular prosthesis (e.g., a stent, stent graft or other endovascular prosthesis) and/or obtaining position sensor space data regarding the endovascular prosthesis. In some embodiments, the system of the invention may include a delivery instrument, and endovascular prosthesis, a tracking system, an imaging modality, a computer system, and a display device. In some embodiments other elements or variations thereof may be used. In some embodiments not all elements may be necessary.

In some embodiments, one or more position indicating elements may be associated with the endovascular prosthesis to obtain detailed position sensor space data regarding the endovascular prosthesis. In some embodiments, one or more of the associated position indicating elements may be selectively movable within the endovascular prosthesis as well as selectively fixable therein, such that the location and/or orientation of the endovascular prosthesis and one or more locations within or around the endovascular prosthesis may be determined in position sensor space. In some embodiments, the one or more position indicating elements used to determine the location of and/or locations within or around the endovascular prosthesis may be movable within a region that may be bounded by the extents of the endovascular prosthesis or otherwise bounded. For example, in some embodiments, the movement of position indicating elements may be constrained by a guidance portion of the endovascular prosthesis such as, for example, held on a strut or rail confined within the endovascular prosthesis.

In some embodiments, the position indicating elements may be constructed to include a hollow core (e.g., an electromagnetic sensor may be constructed as a generally cylindrical wire coil) that is mounted on the strut or rail (e.g., the strut or rail maybe threaded through the hollow portion of the coil) so as to enable the coil to slide along the strut or rail. By sliding a position indicating element on the strut or rail or otherwise moving the sensor between the extrema of the endovascular prosthesis while sampling the location of the position indicating element using the tracking system, part or all of a space or path occupied by the endovascular prosthesis may be determined in position sensor space. Additionally, in some embodiments, the strut or rail or other guidance portion of the endovascular prosthesis may bend or otherwise deform with deformations of the endovascular prosthesis, so that sampling of a position indicating element that moves along the guidance portion may provide a reflection of these deformations.

In some embodiments, a position indicating element may be held in place on the strut or rail until detached via an integrated detachment mechanism.

In some embodiments, a position of the position indicating element used to determine positions in and/or around the endovascular prosthesis may be controlled by mechanical force (e.g., pulling or pushing). For example, a "control line" or other motive portion of endovascular prosthesis may run within a lumen of a delivery instrument and may be used to push or pull the position indicating element from one position to another. The control line may include a wire, tube, or other connector element that serves to move the one or more position indicating elements. A first end (e.g., distal end) of the control line may be connected to the position indicating element, while a second end (e.g., proximal end) of the control line may emerge from a lumen of delivery instrument and such that movement of the second end of the control line translates into movement of the one or more position indicating elements to which it is connected.

In some embodiments, a guidance portion of the endovascular prosthesis (e.g. a rail) may traverse a body portion of the endovascular prosthesis lengthwise so as to provide a path for an associated position indicating element generally along the length of the body portion. In some embodiments, the guidance portion may tortuously traverse the body portion of the endovascular prosthesis height-wise, widthwise and/or lengthwise (e.g., in a spiral pattern) so as to form a path for the position indicating element that generally maps a three dimensional shape of the body portion. In some embodiments, the guidance portion may generally deform when the three dimensional shape of the body portion of the endovascular prosthesis deforms, so that such deformations may be reflected by sampling the position indicating element as it is moved within endovascular prosthesis.

In some embodiments, the invention may include a modification element that may be used to apply material to a positioned endovascular prosthesis. The modification element may include one or more position indicating elements associated therewith such that the modification element can be tracked as it is moved within the anatomy of the patient. In some embodiments, the modification element may weave or otherwise render a coating onto a body portion (e.g., the wall of a body portion) of an endovascular prosthesis. In some embodiments a coating may include a plastic or other material that is deposited or melted onto the endovascular prosthesis through a nozzle of the modification element. In such cases, it may be advantageous to track the location of the nozzle or modification element using its associated position indicating elements and a tracking system so that the material is applied only in regions that require the wall of the endovascular prosthesis to be impermeable, such as for example, the region traversing an aneurysm. In regions outside the aneurysm, the coating need not be applied, so that blood may flow into a secondary vessel for example. In some embodiments, more than one coating type may be applied.

In some embodiments, a precoated endovascular prosthesis may be positioned as described herein and the precoating may be selectively removed using precise location and/or orientation data regarding points within the endovascular prosthesis (e.g., obtained using the systems and methods described herein). For example, in some embodiments, the invention may include a modification element that may be used to remove or otherwise modify material on positioned endovascular prosthesis. The modification element may include one or more position indicating elements associated therewith such that the modification element can be tracked as it is moved within the anatomy of the patient. In one example, removal or modification of material may be accomplished using fiber optically delivered laser energy (the modification element being so equipped). By tracking the location of the fiber using the position indicating elements associated with the modification element, the location of the removed/modified material can be precisely controlled. Many additional methods of selectively removing the material covering the wall of an endovascular prosthesis can also be used including chemical, thermal, mechanical and other methods. In each case, the location of the modification element may be tracked so that the material only in predetermined locations is removed.

In some embodiments, modification elements may include multiple elements that enable multiple features such as, for example, evacuation of debris, curing or mixing of chemicals or drugs, deployment of material, cutting of material, heating, cooling, illuminating, ultrasonically vibrating, injecting or applying other energy to materials, and/or other features or combination thereof. In some embodiments material and/or energy travel through one or more channels or lumens of modification elements of the invention.

In some embodiments, an endovascular prosthesis associated with one or more position indicating elements may be used to facilitate additional treatment or serve as a scaffolding onto which agents may be attached and selectively activated. The location at which the agent is activated may require knowledge of the location of the endovascular prosthesis and its relationship with the surrounding anatomy, both of which can be obtained from an endovascular prosthesis associated with one or more position indicating elements and used with the invention.

In some embodiments, an endovascular prosthesis of the invention may itself be a position indicating element for use within the invention. For example, in some embodiments, an endovascular prosthesis may be fabricated in the form of a coil so that it is capable of receiving electromagnetic fields. This may assist in accurate placement of the endovascular prosthesis, as the location and orientation of the endovascular prosthesis can be more accurately tracked.

In some embodiments, an endovascular prosthesis may be fabricated in place at or near a desired deployment site within the anatomy of a patient. Instead of implanting a pre-assembled endovascular prosthesis the endovascular prosthesis may fabricated within a vessel. In some embodiments, an image guided system may be used to guide a fabrication element having one or more position indicating elements thereon to a desired location in the anatomy of the patient. The endovascular prosthesis may then be fabricated (e.g., woven from nitinol or other shape memory alloy) using the fabrication element. Such internal fabrication may have many advantages such as for example, the dimension of the delivery system be substantially reduced, the location of any applied coating can be controlled and/or other advantages.

In some embodiments, the invention may include a process for using an image guided system to navigate the anatomy of a patient and place and position an endovascular prosthesis, to obtain specific position sensor space information regarding the placed endovascular prosthesis, and/or to perform one or more post placement operations relating to the endovascular prosthesis. In some embodiments, a delivery device equipped with an endovascular prosthesis may be inserted into the anatomy of a patient (e.g., into the vessels of the circulatory system). The endovascular prosthesis may then be navigated to/positioned at a site of interest within the anatomy of the patient (e.g., an aneurism or other position of interest). In some embodiments, this navigation may utilize one or more position indicating elements associated with the delivery device and/or the endovascular prosthesis to enable an image guided system that provides a display of the delivery device and/or the endovascular prosthesis on images of the anatomy of the patient. Furthermore, registrations and/or dynamic referencing may be utilized during such navigation.

In some embodiments, one or more position indicating elements associated with the endovascular prosthesis may be used to obtain position sensor space data regarding one or more points within or around the endovascular prosthesis. This may involve moving the one or more associated position indicating elements within or around the endovascular prosthesis while sampling the location and/or orientation of the one or more associated position indicating elements using a tracking device. In some embodiments, the movement may be actuated using a motive portion of the endovascular prosthesis. In some embodiments, the movement may be constrained by a guidance portion of the endovascular prosthesis.

The obtained position sensor space data may be used for one or more purposes related to the endovascular prosthesis or its location within the anatomy of the patient (e.g., used to add or remove coatings from the endovascular prosthesis, used to re-position the endovascular prosthesis, used to place and/or activate additional devices or elements within or around the endovascular prosthesis, used for dynamic referencing of the anatomy of the patient surrounding the endovascular prosthesis, used for performing a registration of the anatomy of the patient at or near the endovascular prosthesis, or for other purposes).

The various objects, features, and advantages of the invention will be apparent through the detailed description and the drawings attached hereto. It is also to be understood that the following detailed description is exemplary and not restrictive of the scope of the invention.

BRIEF DESCRIPTION OF THE DRAWINGS

FIG. 6 illustrates a process for image guided placement an endovascular prosthesis and determination of locations within an endovascular prosthesis, according to various embodiments of the invention.

DETAILED DESCRIPTION OF PREFERRED EMBODIMENTS

In some embodiments, the system and method of the invention enables tracking of endovascular prostheses and/or patient structures using electromagnetic (EM) or other tracking systems that track one or more position indicating elements. In some embodiments, the invention also enables determination of multiple locations within an endovascular prosthesis through the use of trackable position indicating elements that are selectively movable within the body of an endovascular prosthesis.

In some embodiments, the invention utilizes tracking systems to obtain position sensor space data regarding endovascular prostheses and instrumentation used therewith. This position sensor space data may enable enhanced/accurate placement, deployment, and modification of endovascular prostheses as well as providing other features. For example, in some embodiments, use of a tracking system enables dynamic referencing during placement and deployment of an endovascular prosthesis which may enable correction for breathing motion, cardiac motion, or other motion. Additionally, position sensor space data received from tracking systems may be used for planning purposes, to determine if significant motion exists above a specified threshold that may positively or negatively affect the device, to compensate for motion, and/or for other purposes.

Figure 1:
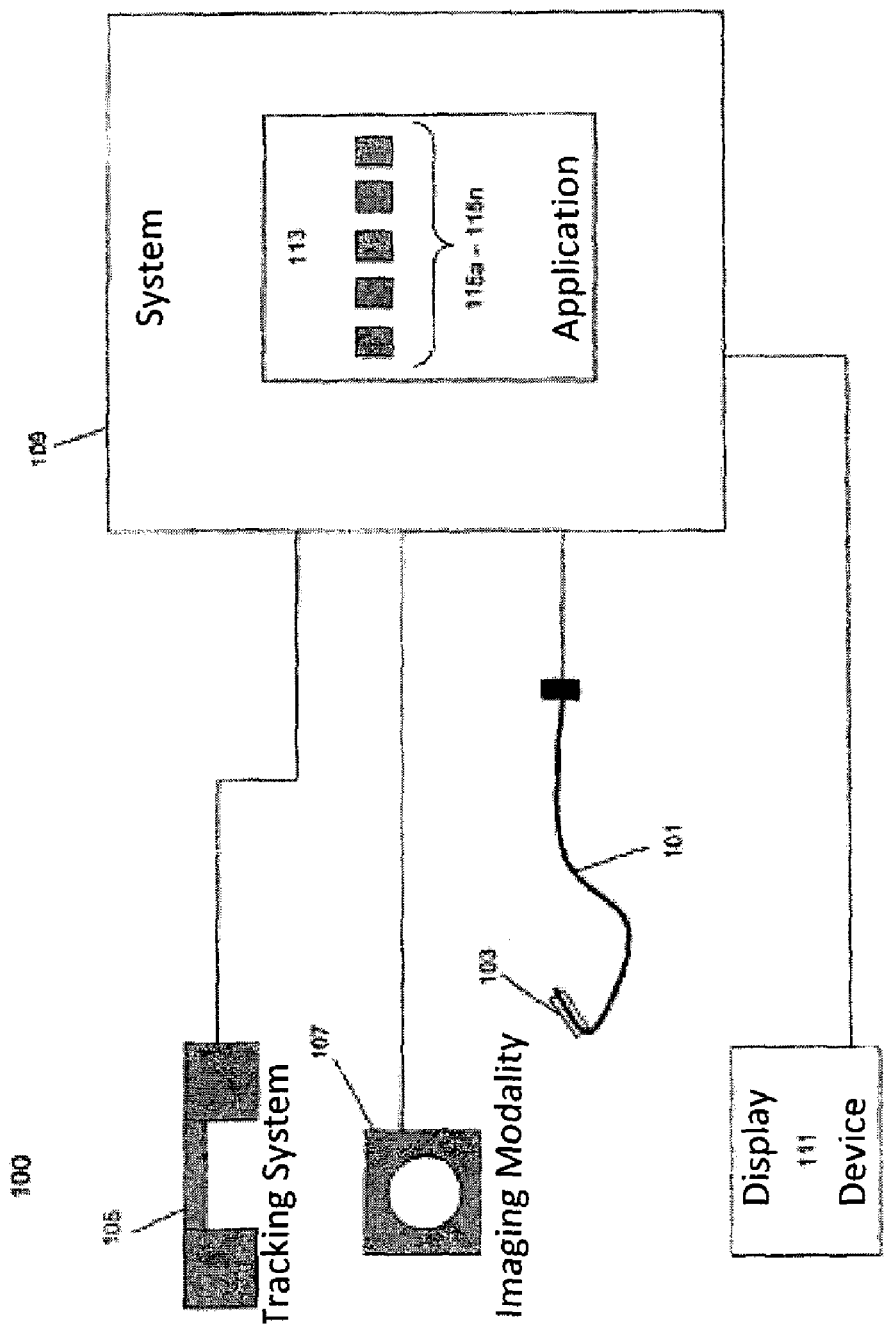
FIG. 1 illustrates an example of a system for image guided placement an endovascular prosthesis and determination of locations within an endovascular prosthesis, according to various embodiments of the invention.

In some embodiments, the invention includes a system for image guided placement and deployment of an endovascular prosthesis (e.g., a stent). FIG. 1 illustrates system 100, which is an example of a system for image guided placement and deployment of an endovascular prosthesis. System 100 may include a delivery instrument 101, and endovascular prosthesis 103, a tracking system 105, an imaging modality 107, a computer system 109, and a display device 111. In some embodiments additional elements may be used. In some embodiments, not all elements may be necessary.

In some embodiments, delivery instrument 101 includes an instrument that may be navigated through vessels in a patient to assist in placement and/or deployment of endovascular prosthesis 103. For example, delivery instrument 101 may include a guidewire that is navigated through the anatomy of the patient and a catheter that is passed over the guidewire through the anatomy of the patient. In some embodiments, the catheter may be or include a endovascular prosthesis deployment catheter with endovascular prosthesis 103 associated therewith. In some embodiments, the catheter may include an intermediate catheter or sheath that may be later exchanged for an endovascular prosthesis delivery catheter.

In some embodiments, Delivery instrument 101 may include one or more lumens for the passage of guidewires or other elements and may include one or more deployment mechanisms for deployment of endovascular prosthesis 103. In some embodiments, delivery instrument 101 may also include radio-opaque fiducials to assist in positioning endovascular prosthesis 103 (see, for example, radio-opaque markings 213 of FIGS. 2A, 2B, and 3).

In some embodiments, system 100 may also include a tracking system 105, which may track the position and/or orientation of one or more position indicating elements in a coordinate system of tracking system 105. For example, in some embodiments, tracking system 105 may include an electromagnetic tracking system that tracks one or more electromagnetic sensor coils as position indicating elements. Tracking system 105 and any associated position indicating element may be used to obtain position sensor space data (also referred to as "patient space data") regarding the location and/or orientation of position indicating elements within anatomical regions of a patient. Obtaining position sensor space data may include tracking system 105 "tracking" or "sampling" one or more position indicating elements used in various embodiments of the invention.

In some embodiments, system 100 may include an imaging modality 107 that is used to obtain one or more images (or image space data) regarding an anatomical region of a patient or elements therein (e.g., instruments, endovascular prosthesis, radio-opaque fiducials, or other elements visible to imaging modality). The image space data may include images taken prior to, during, or after insertion of delivery instrument 101, endovascular prosthesis 103, or other devices or apparatuses into the anatomy of the patient (e.g., "preoperative images"). Image space data may also include intra-operative images or post operative images.

In some embodiments, image space data may be used in conjunction with position sensor space data to perform registration of an anatomical region of a patient, perform dynamic referencing of an anatomical region of a patient, display the location of one or more position indicating elements or associated instruments or devices (e.g., endovascular prosthesis 103) on an image of the anatomy of a patient, display specific points or regions on or within endovascular prosthesis as it exists within an anatomical region of a patient, display the shape or deformations in endovascular prosthesis 103 as it exists within an anatomical region of a patient, or may be used for other purposes.

Information regarding registration, dynamic referencing, and display using merged position sensor space and image space data, and other information may be found in U.S. patent application Ser. No. 11/059,336. (published as U.S. Patent Publication No. 20050182319), filed Feb. 17, 2005, entitled "Method and apparatus for registration, verification, and referencing of internal organs," which is hereby incorporated by reference herein in its entirety. In some embodiments, a registered location and/or orientation of a position indicating element used herein or an instrument associated therewith may be displayed as a moving computer graphic icon overlayed in real-time on a preoperative or intraopeartively captured image or "roadmap." In some embodiments, images may be captured with contrast agents and may include fiducials placed on or in the patient.

In some embodiments, imaging modality 107 may include, a computerized tomography (CT) device, a magnetic resonance (MR) device, a positron emission tomography (PET) device, an X-ray device, a fluoroscopic device, an ultrasound device, or other imaging modality. In some embodiments more than one imaging modality or combinations thereof (e.g., PET/CT, co-registed CT/US, or other combination) may be used. In some embodiments, it may not be necessary to use images or image data.

In some embodiments, system 100 may also include computer system 109, which may be or include one or more computer-implemented devices having one or more processors and associated memory for performing one or more operations related to the reception, storage, transmittal, conversion, registration, superimposition, display, and/or other handling of image space and position sensor space data and/or for other features or functions described herein. Computer system 109 may perform other functions as well. Computer system 109 may include, run, or access application 113 (in some embodiments, multiple applications may be used) and one or more software modules 115a-115n. for enabling performance of the features or functions described herein. Computer system 109 may also include other elements.

In some embodiments, system 100 may include a display device 111, which may include a device (e.g., computer monitor, television monitor, or other monitor) that displays image space data, position space data, a combination of image space and position space data, and/or other data.

As described herein, in some embodiments, system 100 may be used for image guided placement, positioning, and/or deployment of endovascular prosthesis 103. In some embodiments, one or more position indicating elements of system 100 may be used to obtain detailed position sensor space data regarding endovascular prosthesis 103.

In some embodiments, one or more position indicating elements may be associated with endovascular prosthesis 103, delivery instrument 101 and/or other elements of system 100 to assist in placement, positioning, and/or deployment, of endovascular prosthesis 103 and/or to obtain detailed position sensor space data regarding points in and/or around endovascular prosthesis 103. In some embodiments, one or more of the associated position indicating elements may be movable or fixed with respect to delivery instrument 101 and/or endovascular prosthesis 103. In some embodiments, one or more of the associated position indicating elements may be selectively movable within endovascular prosthesis 103 as well as selectively fixable therein. In some embodiments, the associated position indicating elements may be used in combination with radio-opaque fiducials.

In some embodiments, a position indicating element may be fixed to a guidewire that may be selectively fixed within the various portions of delivery instrument 101, including portions coinciding with endovascular prosthesis 103. The position indicating elements on the guidewire may be used to aid in navigating delivery instrument 101 through the anatomy of the patient (e.g., vessel) and/or may be used for other purposes. In some embodiments, once delivery instrument 101 has been routed to the desired place within the anatomy of the patient, the location of endovascular prosthesis 103 can be varied by locking the guidewire and advancing or withdrawing delivery instrument 101.

In some embodiments, one or more position indicating elements may be associated with endovascular prosthesis 103 such that the location and/or orientation of endovascular prosthesis 103 and one or more locations within or around endovascular prosthesis 103 may be determined in position sensor space. In some embodiments, one or more position indicating elements used to determine the location of and locations within or around endovascular prosthesis 103 may be movable within a region that may be bounded by the extents of endovascular prosthesis 103 or otherwise bounded. For example, in some embodiments, the movement of position indicating elements may be constrained by a guidance portion of endovascular prosthesis 103 such as, for example, held on a strut or rail confined within endovascular prosthesis 103.

In some embodiments, the position indicating elements may be constructed to include a hollow core (e.g., an electromagnetic sensor may be constructed as a generally cylindrical wire coil) that is mounted on the strut or rail (e.g., the strut or rail maybe threaded through the hollow portion of the coil) so as to enable the coil to slide along the strut or rail. By sliding a position indicating element on the strut or rail or otherwise moving the sensor between the extrema of endovascular prosthesis 103 while sampling the location of endovascular prosthesis 103 using tracking system 105, part or all of a space or path occupied by endovascular prosthesis 103 (and points in between) may be determined in position sensor space. Additionally, in some embodiments, the strut or rail or other guidance portion of endovascular prosthesis may bend or otherwise deform with deformations of endovascular prosthesis, so that sampling of a position indicating element that moves along the guidance portion may provide a reflection of these deformations.

In some embodiments, a position indicating element may be held in place on the strut or rail until detached via an integrated detachment mechanism. The integrated detachment mechanism may include an electrolytic detachment mechanism, a detachment mechanism utilizing an electrical trigger that induces a magnetic field in the position indicating element to actuate a latch, a detachment mechanism that uses a nitinol (or other shape memory alloy) activated latch, a wire activated latch, or another detachment mechanism. As such, the position indicating element may be selectively placed along the strut or rail and/or, in some embodiments, may be removed or detached from the strut or rail entirely. In some embodiments, a coil comprising the position indicating element may be wound around the strut, and the detachment/retrieval mechanism may apply to an electrical lead wire of the position indicating element as well as, or in place of, the entire position indicating element assembly.

In some embodiments, a position of the position indicating element used to determine positions in and/or around endovascular prosthesis 103 may be controlled by mechanical force (e.g., pulling or pushing). For example, a "control line" or other motive portion of endovascular prosthesis may run within a lumen of delivery instrument 101 and may be used to push or pull the position indicating element from one position to another. The control line may include a wire, tube, or other connector element that serves to move the one or more position indicating elements. A first end (e.g., distal end) of the control line may be connected to the position indicating element, while a second end (e.g., proximal end) of the control line may emerge from a lumen of delivery instrument 101 and such that movement of the second end of the control line translates into movement of the one or more position indicating elements to which it is connected. In one embodiment, a portion of the control line near its second end (i.e., the end not attached to the position indicating element) may include markings representing the distance between extrema of endovascular prosthesis 103 so that when the control line moved a certain distance or is placed in a certain position, the position of the position indicating element within endovascular prosthesis 103 may be determined.

In some embodiments, one or more position indicating elements may be moved within endovascular prosthesis 103 using other motive portions such as, for example, pressure of a fluid that causes one or more position indicating elements to move back and forth, an external magnetic force that may move one or more position indicating elements, or other methods.

Figure 2A:
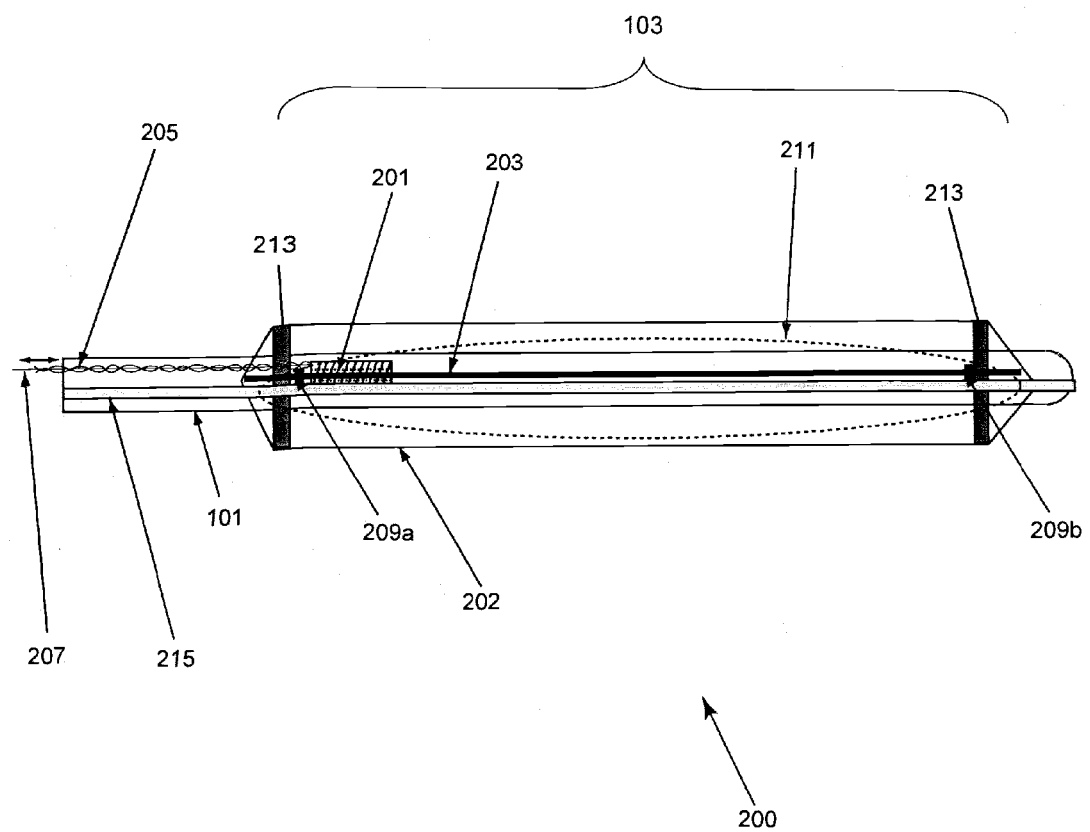
FIGS. 2A and 2B illustrate an example of an assembly wherein a position indicating element is movable within an endovascular prosthesis according to various embodiments of the invention.

FIG. 2A illustrates an assembly 200 which is an example of an assembly for positioning, deploying, and/obtaining detailed position sensor space data regarding endovascular prosthesis 103. Assembly 200 may be part of or used in conjunction with system 100. Assembly 200 may include a hollow-core position indicating element 201 that is arranged such that it may slide along a guidance portion of endovascular prosthesis 103 (illustrated as rail 203, which is an example of a guidance portion of an endovascular prosthesis used in conjunction with the invention). In some embodiments, rail 203 may include end stops 209a. and 209b, which may limit the sliding range of position indicating element 201 along rail 203.

Position indicating element 201 may be connected to tracking device 105 via leadwires 205, although, in some embodiments, the connection/communication between tracking device and position indicating element 201 may be wireless. Position indicating element 201 may be moved along rail 203 via a motive portion of endovascular prosthesis 103, illustrated in FIG. 2A as control line 207 (which is an example of a motive portion of an endovascular prosthesis used in conjunction with the invention). In some embodiments, leadwires 205 may be wrapped around or otherwise associated with control line 207.

In some embodiments, rail 203 may traverse body portion 202 of endovascular prosthesis 103 lengthwise so as to provide a path for position indicating element 201 generally along the length of body portion 202. In some embodiments, rail 203 may bend and/or otherwise deform as body portion 202 of endovascular prosthesis 103 bends and deforms so that these deformations may be reflected by sampling position indicating element 201 as it is moved within endovascular prosthesis 103.

Assembly 200 may include other elements used for the placement of, deployment of, and/or obtaining position sensor space data regarding endovascular prostheses 103 such as, for example, a balloon 211 for expanding an expandable body portion 202 of endovascular prosthesis 103 (for deployment purposes), one or more radio-opaque bands 213, a guidewire lumen 215, and/or other elements. In some embodiments, other lumens or elements (not shown) may be included in delivery instrument 101 in catheter (e.g. a lumen for inflating balloon 211).

Figure 2B:
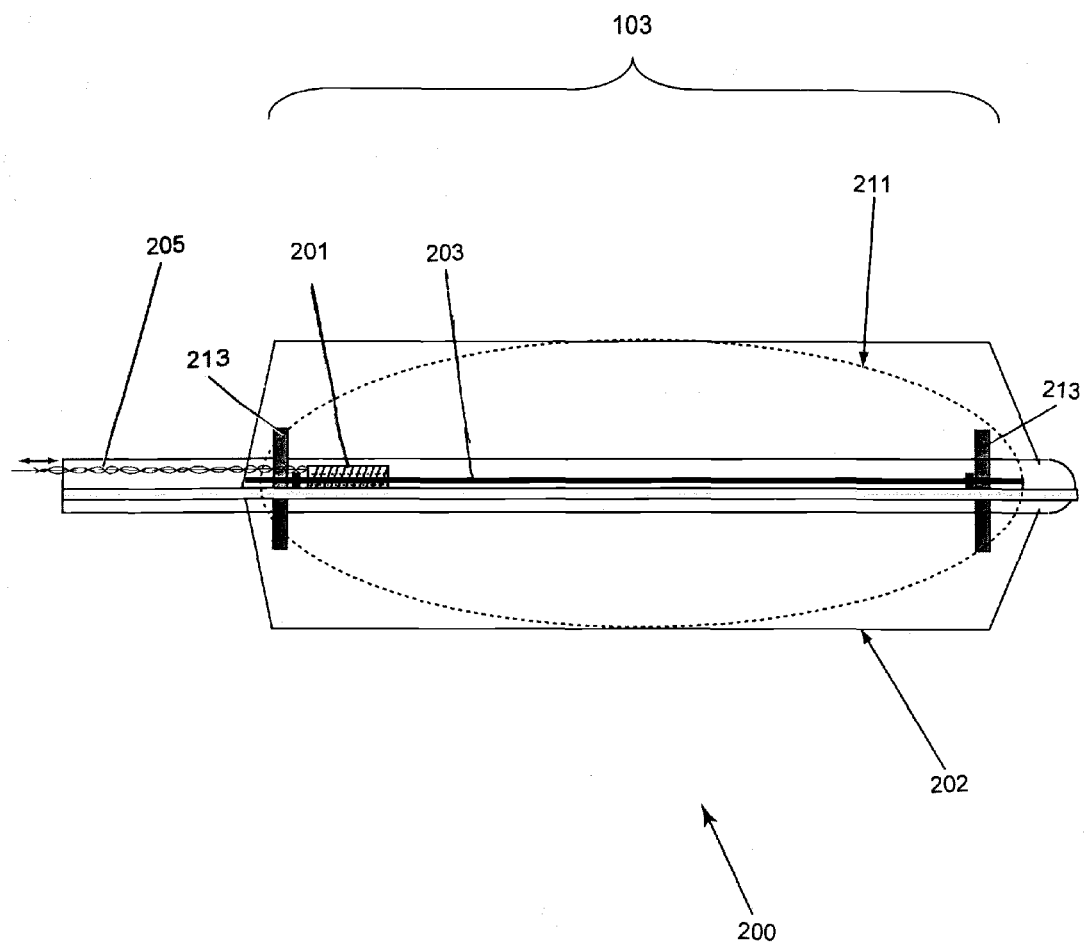

FIG. 2B illustrates assembly 200, wherein balloon 211 is inflated thereby deploying endovascular prosthesis 103 by expanding the expandable body portion 202 of endovascular prosthesis 103.

Figure 3:
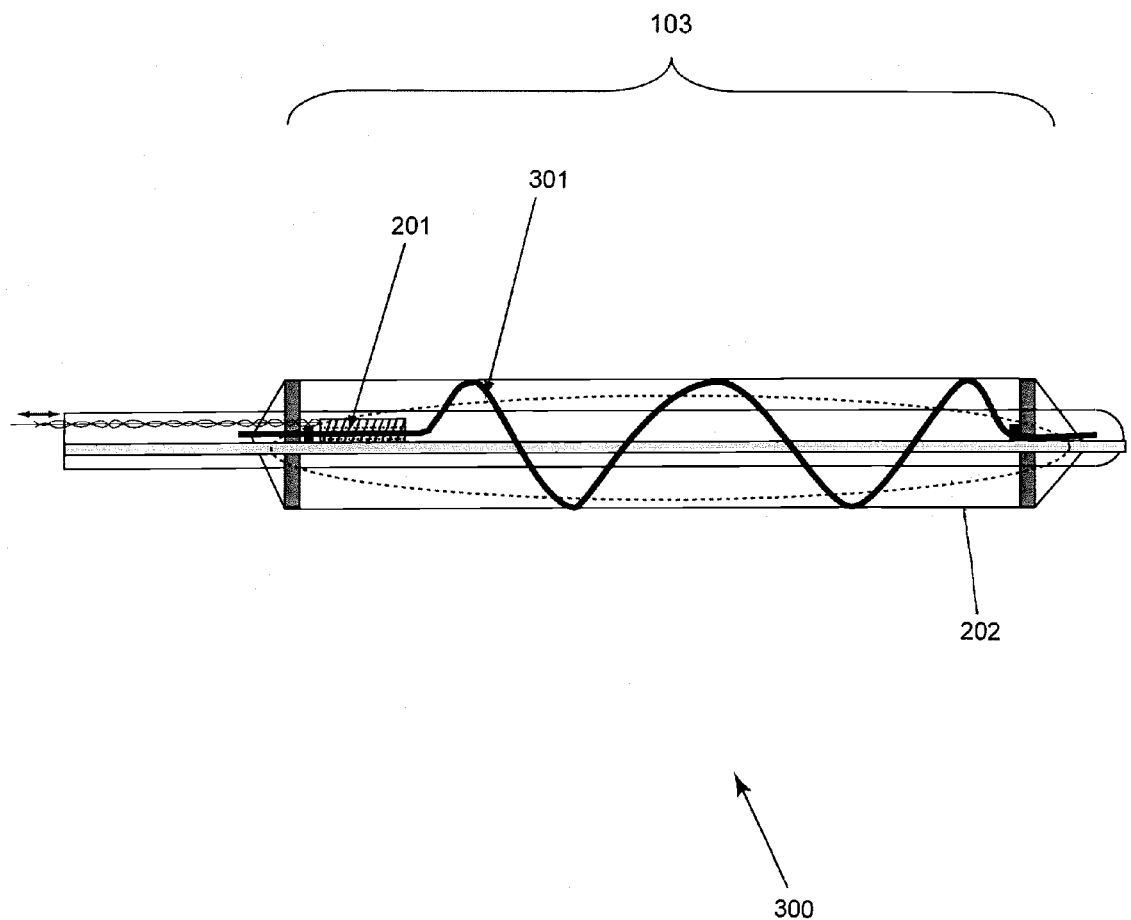
FIG. 3 illustrates an example of an assembly wherein a position indicating element is movable within an endovascular prosthesis according to various embodiments of the invention.

FIG. 3 illustrates an assembly 300, which is an example of an assembly for positioning, deploying, and/obtaining detailed position sensor space data regarding endovascular prosthesis 103, wherein a guidance portion (e.g., rail 301) along which a position indicating element 201 can be slid includes a spiral portion path that corresponds to the interior shape of endovascular prosthesis 103 in its current deployment state. Assembly 300 may be part of or used in conjunction with system 100. By sliding position indicating element 201 along rail 301, a sampling of the complete interior shape and location of endovascular prosthesis 103 can be determined, including its extents.

In some embodiments, rail 301 may tortuously traverse body portion 202 of endovascular prosthesis 103 height-wise, widthwise and/or lengthwise so as to form a path for one position indicating element 201 that generally maps a three dimensional shape of body portion 202. In some embodiments, rail 301 may generally deform when the three dimensional shape of the body portion of the endovascular prosthesis deforms, so that such deformations may be reflected by sampling position indicating element 201 as it is moved within endovascular prosthesis 103.

In some embodiments, the spiral path of a guidance portion (e.g., rail 301) of an endovascular prosthesis according may be an expandable spiral pathway that may be used to determine the shape of an aneurism or other anatomical region of a patient. In these instances, the spiral rail may be located outside the endovascular prosthesis or embedded within it. The spiral rail may be inserted into the anatomical region of interest in an un-expanded or compressed state, and then expanded such that at least a portion of the spiral rail contacts at least a portion of the confines of the surrounding anatomical region. For example, if the expandable rail were placed within a blood vessel having an aneurism therein, the rail would expand to a shape that indicates the presence of the aneurism. By passing the one or more position indicating elements through or along the expanded spiral rail and sampling the position of the position indicating elements, the interior shape of the confines of the surrounding anatomical region that the spiral rail contacts may be determined, for example the interior shape of a vessel or other anatomical region.

Although FIGS. 2A, 2B and 3 illustrate a position indicating element that is slidable along a rail, other configurations may be utilized wherein a position indicating element is confined to a lumen (i.e., another example of a guidance portion) rather than slid on a rail. Other methods of selectively moving position indicating element with respect to an endovascular prosthesis to determine a position of the endovascular prosthesis and/or positions within and around the endovascular prosthesis may be used.

Referring to FIGS. 2A, 2B and 3, in some embodiments, after endovascular prosthesis has been navigated into a desired location of the anatomy of a patient, position indicating element 201 may be moved within endovascular prosthesis as constrained by a guidance portion (e.g. rail 203, 301, or other guidance portion) as the location and/or orientation of position indicating element 201 is tracked/sampled by tracking system 105 so as to provide position sensor space data regarding endovascular prosthesis 103 as is exists within the anatomical region of the patient. As discussed herein, position indicating element 201 may be fixed with respect to endovascular prosthesis 103 and position sensor space data may be obtained and used for, inter alia, navigation of endovascular prosthesis within the anatomy of the patient, dynamic referencing of the anatomy of the patient, and/or other used for other purposes. In some embodiments, position sensor data regarding the location and/or orientation of an endovascular prosthesis and/or locations within and around the endovascular prosthesis may be used in conjunction with image space data regarding the anatomical region in which the endovascular prosthesis is to be deployed to display the location and/or orientation of the endovascular prosthesis and/or the location of the extents of the endovascular prosthesis on a display screen (e.g., display screen 111).

As mentioned herein, in some embodiments, system 100 and/or elements thereof (including position indicating elements) may be used to perform registration and/or other functions. For example, in some embodiments, one or more position indicating elements that are trackable via tracking system 105 may be movable over the length of delivery instrument 101, enabling a registration to be performed along the path of delivery instrument 101. In this instance, the position indicating elements may not be confined to positions within endovascular prosthesis 103. For example, a control line used to manipulate the position of a position indicating element may be used to draw the position indicating element down a pathway of a lumen of delivery device 101. In some embodiments, the lumen used for this manipulation/movement of position indicating elements may be coaxial to a lumen used for deployment of endovascular device 103. However, in some embodiments, these lumens may be the same lumen, tandem lumens, or arranged in a nested or endoluminal fashion. Additional information relating to registration and other information can be found in U.S. Pat. No. 6,785,571, entitled "Device and method for registering a position sensor in an anatomical body," which is hereby incorporated by reference herein in its entirety.

In some embodiments, a registered location and/or orientation of the position indicating element associated with an endovascular prosthesis according to the invention may be displayed as a moving computer graphic icon overlayed in real-time on a preoperative or intra-operatively captured image or "roadmap" constructed using image space data obtained from an imaging modality (e.g., imaging modality 107). In some embodiments, images may be captured with contrast agents and may include fiducials (e.g., radio opaque fiducials 213) placed on or in the patient.

In some instances, stents or other endovascular prostheses may be pre-coated with material that aids in their operation or provides other advantages. However, in some embodiments, instead of a pre-coated endovascular prosthesis, a bare or non-coated endovascular prosthesis may be positioned in the anatomy of a patient (e.g., using system 100 and the assemblies illustrated herein). Thereafter, a coating may be selectively applied in place. The coating may be selectively applied using precise location and/or orientation data regarding points within the endovascular prosthesis (e.g., obtained using the systems and methods described herein). This modification may be made pre or post deployment. For example, in some embodiments, system 100 may include a modification element (not illustrated in FIG. 1) that may be used to apply material to a positioned endovascular prosthesis. The modification element may include one or more position indicating elements associated therewith such that the modification element can be tracked and displayed by system 100 as it is moved within delivery device 101 and/or endovascular prosthesis 103. In some embodiments, the modification element may weave or otherwise render a coating onto a body portion (e.g., the wall of a body portion) of an endovascular prosthesis. In some embodiments, the modification element may utilize a plastic or other material that can be deposited or melted onto the endovascular prosthesis through a nozzle of the modification element. In such cases, it may be advantageous to track the location of the nozzle or modification element via its associated position indicating elements so that the material is applied only in regions that require the wall of the endovascular prosthesis to be impermeable, such as for example, the region traversing an aneurysm. In regions outside the aneurysm, the coating need not be applied, so that blood may flow into a secondary vessel for example. In some embodiments, more than one coating type may be applied.

For example, an adhesive may be applied at the ends of the endovascular prosthesis to cause it to be strongly fixed to a vessel wall. A second coating may then be applied that covers a graft region that provides fluidic impermeability to relieve pressure on the endovascular prosthesis.

In some embodiments, one or more of the applied coatings may be biologically active, may contain anti clotting agents, may contain substances that impede tissue ingrowth into a lumen of the endovascular prosthesis, may contain biodegradable substances, or may have other properties. In one example, the edges of any graft or stent graft of PTFE may be soaked in pro-endothelialization materials, such that the free edges of the stent or stent graft will be adopted by the native endothelium of the vessel in a more natural and rapid way, decreasing the risk for endoleak. This pro-endotheilialization substance can be any pro-endothelial factor such as endothelial growth factor, vascular endothelial growth factor (VEGF) or any related compound. The use of a pro-endothelialization material may helpful in the setting of traumatic aortic injury, where patients may be younger, without as much risk for atherosclerosis in the near term as a complication of the soaking elements near the implantation site.

In some embodiments, a precoated endovascular prosthesis may be positioned as described herein and the precoating may be selectively removed or modified using precise location and/or orientation data regarding points within the endovascular prosthesis (e.g., obtained using the systems and methods described herein). For example, in some embodiments, system 100 may include a modification element (not illustrated in FIG. 1) that may be used to remove or otherwise modify material on positioned endovascular prosthesis. The modification element may include one or more position indicating elements associated therewith such that the modification element can be tracked and displayed by system 100 as it is moved within delivery device 101. In one example, removal or modification of material may be accomplished using fiber optically delivered laser energy (the modification element being so equipped). By tracking the location of the fiber using the position indicating elements associated with the modification element, the location of the removed/modified material can be precisely controlled. Many additional methods of selectively removing the material covering the wall of an endovascular prosthesis can also be used including chemical, thermal, mechanical, and/or other methods. In each case, the location of the modification element may be tracked so that the material only in predetermined locations is removed.

Figure 4:
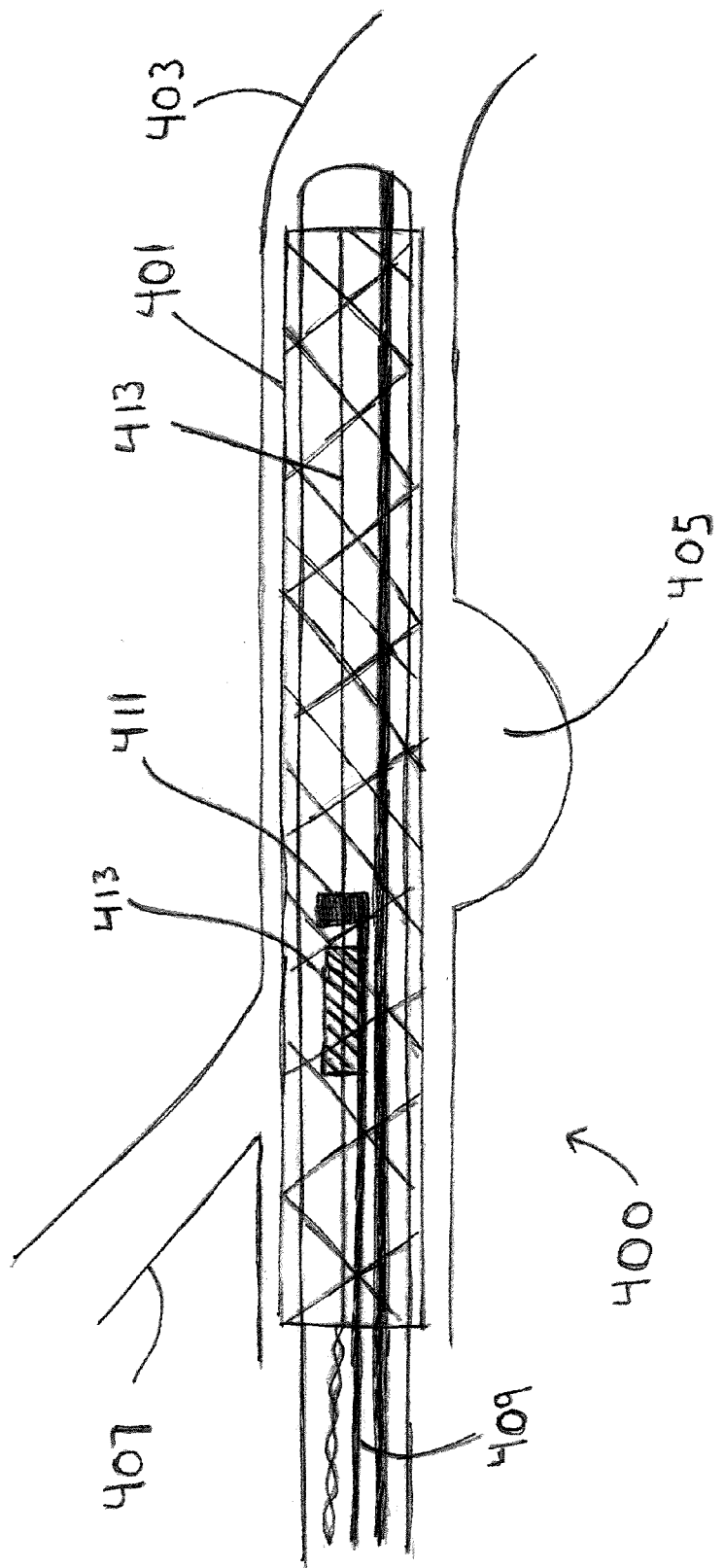
FIG. 4 illustrates an example of an assembly wherein a modification element is guided to specific locations of an endovascular prosthesis according to various embodiments of the invention.

FIG. 4 illustrates an assembly 400 which is an assembly for selectively modifying a positioned endovascular prosthesis 401 according to various embodiments of the invention. Assembly 400 may be used with system 100 or other image-guided systems as described herein. As illustrated, in FIG. 4, endovascular prosthesis 401 is shown in an unexpanded/undeployed state. Endovascular prosthesis 401 is positioned in a vessel 403 that exhibits a bulging aneurism 405 and that includes a branch vessel 407. As illustrated in FIG. 4, the body portion of endovascular prosthesis 401 covers the opening of branch vessel 407. If an endovascular prosthesis fully coated with an impermeable material were deployed in this location, branch vessel 407 would be occluded, potentially leading to complications. As such, it may be desirable to ensure that the opening to branch vessel 407 is not covered by an endovascular prosthesis that includes an impermeable material.

As such, assembly 400 includes a modification element 409 having a nozzle portion 411 and a position indicating element 413 that is in a known relationship with nozzle portion 411. As such, if endovascular prosthesis 401 were entirely precoated and modification element 409 and nozzle 411 were equipped so as to remove the precoating (e.g., ablation, heating, chemical reaction, physical stripping or other removal methods), the precoating may be selectively removed at the opening to branch vessel 407, while leaving the precoating in the region of aneurism 405. As nozzle portion 411 is in a known relationship with trackable position indicating element 413, the removal of precoating may be precisely controlled.

In another example, if endovascular prosthesis 401 included no coating and modification element and nozzle portion 411 were equipped to apply such a coating (e.g., a polymer, epoxy or other material such as those currently employed in rapid prototyping techniques), nozzle 411 may be used to apply the coating to the region of aneurism 405 and/or other desired regions while not applying the coating to the opening of branch vessel 407. Again, as nozzle 411 is in a known relationship with trackable position indicating element 413, the application of coating may be precisely controlled.

In some embodiments, position sensor space data regarding specific locations within endovascular prosthesis 401 obtained using the methods and systems described herein may be used to precisely identify/define the regions where modification of endovascular prosthesis 401 is necessary, further enhancing the precision of such procedures. For example, if endovascular prosthesis 401 included a movable position indicating element such as that illustrated in FIGS. 2A, 2B, or 3, the precise location on the body portion of the endovascular prosthesis where aneurism 405 or the opening to branch vessel 407 exists can be defined in image sensor space prior to introducing modification element into the interior of endovascular prosthesis 401 for modification.

In some embodiments, movement of modification element 409 may be constrained by a guidance portion 415 of endovascular prosthesis 401 (e.g., a rail, or other guidance portion such as, for example, those illustrated in FIGS. 2A, 2B, or 3).

In some embodiments, position indicating element 413 may be used to determine the relative spatial orientation and location of nozzle portion 411 relative to the underlying anatomy of the patient. In some embodiments, a registration process may be performed that enables the display of the position and orientation of nozzle portion 411 relative to the underlying anatomy of the patient. In some embodiments, position indicating element 413 may itself be used to perform a modification function such as, for example, delivering energy through local heating.

In some embodiments, modification elements may include multiple elements that enable multiple features such as, for example, evacuation of debris, curing or mixing of chemicals or drugs, deployment of material, cutting of material, heating, cooling, illuminating, ultrasonically vibrating, injecting or applying other energy to materials, and/or other features or combination thereof. In some embodiments material and/or energy may travel through one or more channels or lumens of modification elements of the invention.

In some embodiments, an endovascular prosthesis associated with one or more position indicating elements, may be used to facilitate additional treatment or serve as a scaffolding onto which agents may be attached and selectively activated. The location at which the agent is activated may require knowledge of the location of the endovascular prosthesis and its relationship with the surrounding anatomy, both of which can be obtained from an endovascular prosthesis associated with one or more position indicating elements and used with system 100 or other system of the invention. For example, heat shock protein promoters (HSP-70. promoters for example) can serve as a trigger switch—activating deployment of a gene product or plasmid when the substance is exposed to heat. The activated gene product or plasmid can then have a local effect.

Using position indicating elements that may be present on the endovascular prosthesis in combination with position indicating elements that may be present on additional elements/device, their activation devices, and/or their delivery devices, the additional elements/devices may be selectively deployed or activated in precise locations. Additionally, if the anatomy of the patient has been registered with position indicating element of the endovascular prosthesis, the relative location in the anatomy that specific activation will occur can be pre-selected.

Figure 5:
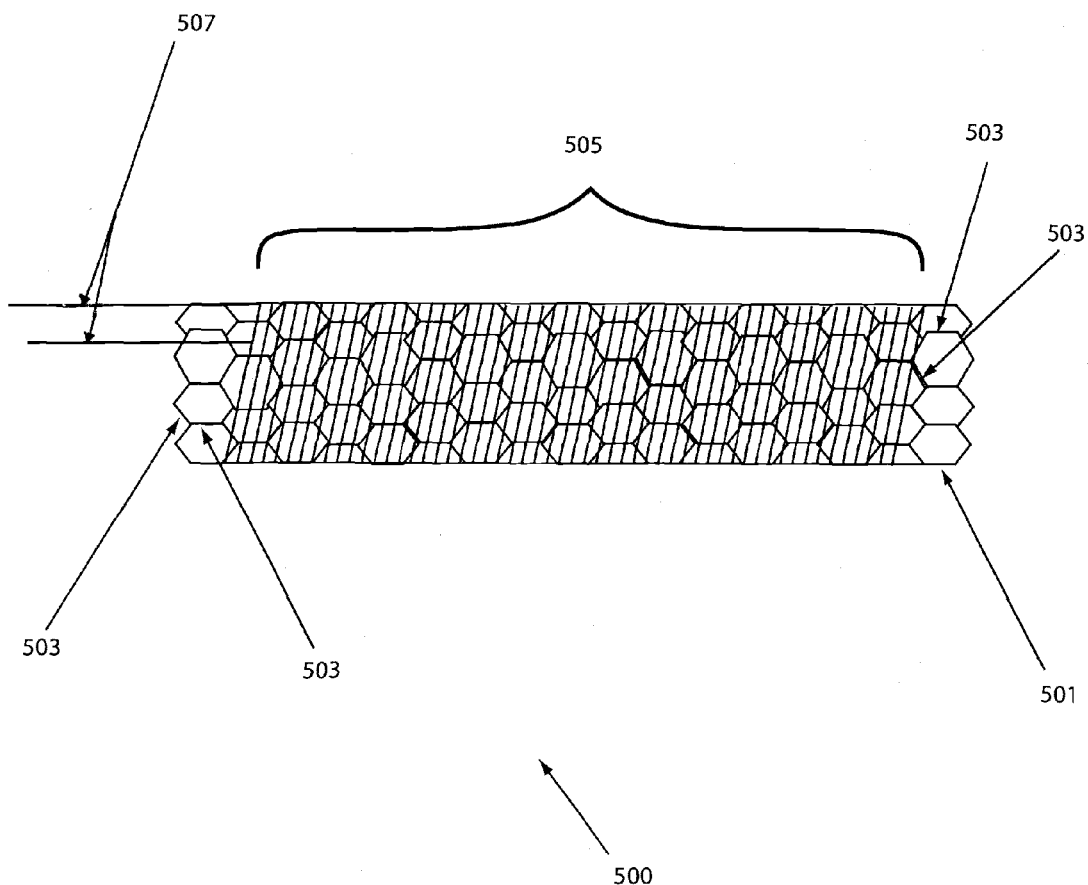
FIG. 5 illustrates an example of an endovascular prosthesis that acts as a position indicating element according to various aspects of the invention.

In some embodiments, an endovascular prosthesis of the invention may itself be a position indicating element for use within system 100. For example, in some embodiments, an endovascular prosthesis may be fabricated in the form of a coil so that it is capable of receiving electromagnetic fields. This may assist in accurate placement of the endovascular prosthesis, as the location and orientation of the endovascular prosthesis can be more accurately tracked. FIG. 5 illustrates an endovascular prosthesis 500, having an expandable body portion 501 that includes structural support members 503. Endovascular prosthesis 500 may also include coil windings 505 that enable endovascular prosthesis 500 to be tracked by a tracking system (tracking system 105). In some embodiments, coil windings 505 may be wound inside structural support members 503, outside of structural support members 503, interwoven between structural support members 503, or otherwise integrated with structural support members 503. As body portion 501 and structural support members 503 may be expandable so as to deploy endovascular prosthesis 500 within the anatomy of a patient, coil windings 505 may also be expandable and as such may expand with body portion 501. Endovascular prosthesis may also include lead wires 507 to connect endovascular prosthesis 500 to its associated tracking device. In some embodiments, endovascular prosthesis 500 may communicate wirelessly with its associated tracking system. As such, lead wires 507 may not be present. In some embodiments, lead wires 507 may be removable (e.g., for removal after deployment of endovascular prosthesis 500).

In some embodiments, an endovascular prosthesis may be fabricated in place at a or near a desired deployment site within the anatomy of a patient. Instead of implanting a pre-assembled endovascular prosthesis the endovascular prosthesis may fabricated within a vessel. In some embodiments, an image guided system (e.g., system 100) may be used to guide a fabrication element having one or more position indicating elements thereon to a desired location in the anatomy of the patient. The endovascular prosthesis may then be fabricated (e.g., woven from nitinol or other shape memory alloy) using the fabrication element. Such internal fabrication may have many advantages such as for example, the dimension of the delivery system be substantially reduced, the location of any applied coating can be controlled and/or other advantages.

FIG. 6 illustrates a process 600, which is an example of a process for using an image guided system (e.g., system 100) to navigate the anatomy of a patient and place or position an endovascular prosthesis, to obtain specific position sensor space information regarding the placed endovascular prosthesis, and/or to perform one or more post placement operations relating to the endovascular prosthesis. In an operation 601 a delivery device 601 (e.g., delivery device 101) equipped with an endovascular prosthesis (e.g., endovascular prosthesis 103) may be inserted into the anatomy of a patient (e.g., into the vessels of the circulatory system).

In an operation 603, the endovascular prosthesis may be navigated to/positioned at a site of interest within the anatomy of the patient (e.g., an aneurism, such as the one illustrated in FIG. 4). This navigation may utilize one or more position indicating elements associated with the delivery device and/or the endovascular prosthesis to enable an image guided system (e.g., system 100) that provides a display of the delivery device and/or the endovascular prosthesis on images of the anatomy of the patient. Furthermore, registrations and/or dynamic referencing may be utilized during such navigation.

In an operation 605, one or more position indicating elements associated with the endovascular prosthesis may be used to obtain position sensor space data regarding one or more points of the endovascular prosthesis (e.g., such as enabled by system 100, and assembly 200, 300, or 400). This may involve moving the one or more associated position indicating elements within or around the endovascular prosthesis while sampling the location and/or orientation of the one or more associated position indicating elements at one or more points within the endovascular prosthesis using a tracking device (e.g., tracking device 105).

In an operation 607, the position space data may be used for one or more purposes related to the endovascular prosthesis or its place within the anatomy of the patients (e.g., used to add or remove coatings from the endovascular prosthesis, used to re-position the endovascular prosthesis, used to place and/or activate additional devices or elements within or around the endovascular prosthesis, used for dynamic referencing of the anatomy of the patient surrounding the endovascular prosthesis, used for performing a registration of the anatomy of the patient at or near the endovascular prosthesis, or for other purposes).

In some embodiments, additional operations may be utilized to perform the processes or methods of the invention described herein. In some embodiments, not all operations are necessary. In some embodiments, the order or operations described herein may be varied.

Other embodiments, uses and advantages of the invention will be apparent to those skilled in the art from consideration of the specification and practice of the invention disclosed herein. The specification should be considered exemplary only, and the scope of the invention is accordingly intended to be limited only by the following claims.

What is claimed is:

1. A system for obtaining position data regarding an endovascular prosthesis within an anatomical region of a patient, the system comprising:
   a tracking system including a coordinate system;
   at least one position indicating element whose location is tracked by the tracking system for providing position data regarding a location of the at least one position indicating element in the coordinate system of the tracking system;
   the endovascular prosthesis having an expandable body portion, wherein the at least one position indicating element is movable within the expandable body portion of the endovascular prosthesis;
   a guidance portion that constrains movement of the at least one position indicating element within the expandable body portion of the endovascular prosthesis; and
   a motive portion that moves the at least one position indicating element within the expandable body portion of the endovascular prosthesis while the at least one position indicating element is tracked to produce position data regarding at least two points within the expandable body portion of the endovascular prosthesis, wherein the at least two points indicate the position data at which the at least one position indicating element is constrained by the guidance portion, wherein the tracking system comprises an electromagnetic tracking system, the at least one position indicating element comprises at least one electromagnetic sensor coil having a hollow interior portion, the guidance portion includes a rail, and the electromagnetic sensor coil is mounted on the rail through the hollow interior portion such that the electromagnetic sensor coil slides along the rail.

2. The system of claim 1, wherein the guidance portion includes a straight line portion that axially traverses the expandable body portion of the endovascular prosthesis lengthwise and forms a path for the at least one position indicating element generally along a length of the expandable body portion of the endovascular prosthesis, and wherein the straight line portion generally deforms in accordance with deformations in the expandable body portion of the endovascular prosthesis.

3. The system of claim 1, wherein the guidance portion includes a spiral portion to tortuously traverse the expandable body portion of the endovascular prosthesis height-wise, widthwise and lengthwise and to form a path for the at least one position indicating element that generally maps a three dimensional shape of the expandable body portion of the endovascular prosthesis, and wherein the spiral portion generally deforms when the three dimensional shape of the expandable body portion of the endovascular prosthesis deforms.

4. The system of claim 1, wherein the guidance portion comprises a lumen within the expandable body of the endovascular prosthesis through which the at least one position indicating element moves.

5. The system of claim 1, wherein the motive portion comprises a control wire having a first end and a second end, wherein the first end of the control wire is attached to the at least one position indicating element, and wherein movement of the second end translates into movement of the at least one position indicating element within the expandable body portion of the endovascular prosthesis as constrained by the guidance portion.

6. The system of claim 1, wherein the at least two points at least partially define a region where material is added to or removed from the expandable body portion of the endovascular prosthesis.

7. The system of claim 6, further comprising a modification device having at least two position indicating elements tracked by the tracking system, wherein the modification device is positioned at the region where the material is added to or removed from the expandable body portion of the endovascular prosthesis.

8. The system of claim 1, wherein the at least one position indicating element is constrained within the endovascular prosthesis and provides position data regarding location of the endovascular prosthesis as the endovascular prosthesis is navigated within the anatomical region of the patient.

9. The system of claim 1, wherein the at least one position indicating element is constrained within the endovascular prosthesis and provides position data regarding movement of the anatomical region of the patient from tracked movement of the at least one position indicating element within the anatomical region of the patient.

10. A method for obtaining position data regarding an endovascular prosthesis within an anatomical region of a patient, the method comprising the acts of:

positioning an endovascular prosthesis device having an expandable body portion equipped with at least a one position indicating element into the anatomical region of the patient;

tracking the at least one position indicating element by a tracking system to provide position data regarding a location of the at least one position indicating element in a coordinate system of the tracking system;

moving the at least one position indicating element within the expandable body of the endovascular prosthesis;

constraining a movement of the at least one position indicating element by a guidance portion of the endovascular prosthesis; and sampling, using the tracking system, position data regarding the at least one position indicating element in at least two points within the expandable body portion of the endovascular prosthesis, wherein the at least two points indicate the position data at which the at least one position indicating element is constrained by the guidance portion, wherein the tracking system comprises an electromagnetic tracking system, wherein the at least one position indicating element comprises at least one electromagnetic sensor coil having a hollow interior portion, wherein the guidance portion includes a rail, and wherein the electromagnetic sensor coil is mounted on the rail through the hollow interior portion such that moving the at least one position indicating element within the expandable body of the endovascular prosthesis further comprises sliding the electromagnetic sensor coil along the rail.

11. The method of claim 10, wherein the guidance portion includes a straight line portion that axially traverses the expandable body portion of the endovascular prosthesis lengthwise and forms a path for the at least one position indicating element generally along a length of the expandable body portion of the endovascular prosthesis, and wherein the straight line portion generally deforms in accordance with deformations in the expandable body portion of the endovascular prosthesis.

12. The method of claim 10, wherein the guidance portion includes a spiral portion to tortuously traverse the expandable body portion of the endovascular prosthesis height-wise, widthwise and lengthwise and to form a path for the at least one position indicating element that generally maps a three dimensional shape of the expandable body portion of the endovascular prosthesis, and wherein the spiral portion generally deforms when the three dimensional shape of the expandable body portion of the endovascular prosthesis deforms.

13. The method of claim 10, wherein the guidance portion comprises a lumen within the expandable body of the endovascular prosthesis through which the at least one position indicating element moves.

14. The method of claim 10, wherein the moving act further comprises the act of moving a control wire having a first end and a second end, wherein the first end of the control wire is attached to the at least one position indicating element, and wherein movement of the second end translates into movement of the at least one position indicating element within the expandable body portion of the endovascular prosthesis as constrained by the guidance portion.

15. The method of claim 10, wherein the at least two points at least partially define a region where material is added to or removed from the expandable body portion of the endovascular prosthesis.

16. The method of claim 15, further comprising the act of positioning a modification device having at least two position indicating elements tracked by the tracking system at the region where the material is added to or removed from the expandable body portion of the endovascular prosthesis.

17. The method of claim 10, wherein the positioning act further comprises the act of constraining the at least one position indicating element within the endovascular prosthesis and providing space data regarding location of the endovascular prosthesis as the endovascular prosthesis is positioned within the anatomical region of the patient.

18. The method of claim 10, further comprising the act of constraining the at least one position indicating element within the endovascular prosthesis and providing position data regarding movement of the anatomical region of the patient from tracked movement of the at least one position indicating element within the anatomical region of the patient.

19. A system for obtaining space data regarding an endovascular prosthesis within an anatomical region of a patient, the system comprising:

a tracking system including a coordinate system;

at least one position indicating element that includes a plurality of coil windings, wherein the at least one position indicating element is tracked by the tracking system that provides position sensor space data regarding a location of the at least one position indicating element in a coordinate system of the tracking system;

an endovascular prosthesis having an expandable body portion that includes structural support members; and a guidance portion that constrains movement of the at least one position indicating element within the expandable body portion of the endovascular prosthesis;

wherein the at least one position indicating element is movable to at least two points constrained within the expandable body portion of the endovascular prosthesis, and wherein at least a portion of the plurality of coil windings is integrated with the structural support members of the expandable body portion such that the plurality of coil windings expands with the structural support members, wherein the guidance portion includes a rail, and wherein the plurality of coil windings is mounted on the rail through a hollow interior portion of the plurality of coil windings such that moving the at least one position indicating element within the expandable body of the endovascular prosthesis further comprises sliding the plurality of coil windings along the rail.

* * * * *